US005957876A

United States Patent [19]

D'Amico

[11] Patent Number: 5,957,876

[45] Date of Patent: Sep. 28, 1999

[54] TRACTION DEVICE FOR PHYSICAL THERAPY

[76] Inventor: Anthony T. D'Amico, 362 Eckford, Troy, Mich. 48084

[21] Appl. No.: 08/906,663

[22] Filed: Aug. 7, 1997

Related U.S. Application Data

[63] Continuation-in-part of application No. 08/426,938, Apr. 21, 1995, abandoned.

[51] Int. Cl.[6] .......... A61F 5/00

[52] U.S. Cl. .......... 602/33; 602/34; 602/242

[58] Field of Search .......... 602/32–36, 38, 602/40; 606/241, 242; 178/DIG. 15; 5/621, 622

[56] References Cited

U.S. PATENT DOCUMENTS

| | | | |
|---|---|---|---|
| Re. 32,791 | 11/1988 | Saunders | 128/75 |
| 2,954,026 | 9/1960 | Spinks | 128/75 |
| 3,003,498 | 10/1961 | Hotas . | |
| 3,105,489 | 10/1963 | Zivi | 128/75 |
| 3,114,366 | 12/1963 | Maychark | 602/33 X |
| 3,149,630 | 9/1964 | Schmidt | 602/36 |
| 3,667,457 | 6/1972 | Zumaglini . | |
| 3,871,366 | 3/1975 | Cotrel | 602/33 |
| 3,905,359 | 9/1975 | Fanstone | 602/32 |
| 4,166,459 | 9/1979 | Nightingale | 128/75 |
| 4,593,684 | 6/1986 | Graham | 128/75 |
| 4,606,333 | 8/1986 | Graham | 128/75 |
| 4,674,485 | 6/1987 | Swanson | 128/75 |
| 4,784,122 | 11/1988 | Graham | 128/75 |
| 4,881,728 | 11/1989 | Hunter | 5/622 |
| 4,971,043 | 11/1990 | Jones | 128/75 |
| 5,129,881 | 7/1992 | Pope | 602/32 |
| 5,146,641 | 9/1992 | Zwickey | 5/628 |
| 5,147,287 | 9/1992 | Jewell et al. | 602/32 |
| 5,177,823 | 1/1993 | Riach | 5/636 |
| 5,181,904 | 1/1993 | Cook et al. | 602/32 |

*Primary Examiner*—Richard J. Apley
*Assistant Examiner*—Denise Pothier
*Attorney, Agent, or Firm*—Young & Basile, P.C.

[57] ABSTRACT

A cervical traction device which can be used on a support surface such as a bed which applies a tractive force to the back of the patient's skull approximate to the occipital bone through the use of contoured blocks which can preferably be positioned behind the patient's head and mounted on a head rest assembly. The tractive force can be administered in a continuous cyclical or intermittent manner controlled by the patient during a cervical traction session. The device has an integrated damping system which permits return of tractive force to the patient during each cycle in a gradual fashion. This gradual return enables this unit to closely simulate cyclic, and cyclic intermittent traction performed in the more expensive in-office equipment used by physical therapists. The head rest assembly slides on the bed or similar surface and can be vertically and laterally adjusted to vary the flexion-extension angle. The cervical traction device can be operated by the patient with or without the help of a second party. The mechanism is configured with gas springs to control the rate of descent of the weight and apply a constant tractive force to the patient in a manner which maximizes safety.

28 Claims, 8 Drawing Sheets

TRACTION DEVICE FOR PHYSICAL THERAPY

CROSS-REFERENCE TO RELATED APPLICATIONS

This application is a continuation-in-part of Ser. No. 08/426,938 filed Apr. 21, 1995, now abandoned.

BACKGROUND OF THE INVENTION

1. Field of the Invention

The present invention is related to physical therapy devices. More particularly, the present invention is related to devices for administering cervical traction to the neck region of a patient. Even more particularly, the present invention is related to cervical traction devices for home-use which provide the option of administering cervical traction in a cyclical, intermittent or non-cyclical manner.

2. Description of Relevant Art

The need for simple, low cost cervical traction devices which can be used at home to administer cervical traction to provide relief to patients with various musculo-skeletal disorders of the neck and back is well recognized. Heretofore there have been developed a great number of head halters or other devices which apply cervical traction through the head of the patient. Many of these devices engage the jaw of the patient while surrounding the head. These type of halters not only inhibit the ability of the patient to talk, they also cause aggravation of the temporomandibular (TMJ) points. As a device for administering cervical traction, these devices are less than desirable. Jaw-type head halters of this type pull from an axis offset from the spine and thereby apply an undesirable twisting moment (cervical extension) to the patient's head and neck contrary to most types of desired cervical traction. In most types of cervical traction situations, it is desirable to engage the head of the patient at the occipital area of the head rather than the chin so that the pulling axis is in straight alignment with the spine and so that the pulling force is concentrated along the posterior of the head where it is most beneficial.

Other types of devices for engaging the head to correct neck problems are cervical braces. Such braces, which are referred to as "halo type", actually contact the patient's head with pointed screws which are forced inward through the skin to make contact with the bone of the skull. Aside from the obvious pain which a patient must endure when this type of brace is employed, the potential for infection to the person's head at the points where the skin is broken is ever present.

In order to obtain effective cervical traction, heretofore, it has been necessary to go to a physical therapy department or office. At such locations cervical traction was applied using complex devices such as that described in U.S. Pat. No. 4,508,109 to Saunders which was reissued as U.S. Pat. No. RE 32,791. Such devices could be used to apply cervical traction. However, they were of limited value because their complexity meant that traction therapy was available to the patient only at limited locations where such devices could be permanently installed. As a result, the patient was able to obtain cervical traction less often than would have been desirable not only because of the inconvenience of having to go to such locations at only the appointed times but also because of the expense.

Therefore, it is highly desirable to provide a cervical traction device applying tractive force in a manner heretofore only available in a physical therapist's office which can be used by the patient at home at various intervals throughout the day so that the patient, with or without assistance, can receive the equivalent therapeutic benefits associated with more frequent cervical traction use. Unfortunately, many cervical traction devices for home use which have been developed previously are either extremely cumbersome, rely on jaw-type head halters, or fail to provide sufficient cervical traction force in a safe manner to be truly beneficial to the patient. Examples of such devices include U.S. Pat. Nos. 4,971,043 to Jones; 5,129,881 to Pope; 3,105,489 to Zivi; 4,674,485 to Swanson; and 2,954,026 to Spinks. Furthermore, none of the cervical traction devices for home use offer an effective tension cycling option.

Thus, it would be beneficial to provide a cervical traction device for use in the home which would provide cervical traction force through the skull proximate to the occiput region in a safe and easy manner which could be used by the patient in a supine position with minimal or no assistance from third parties. It is also desirable that the device provide maximum cervical traction force in a manner which is safe and beneficial to the patient-user. It is also desirable to provide a cervical traction device and method for using the same which enables the patient-user control over the course of physical therapy and its administration in concert with a program recommended by his or her physician and physical therapist.

SUMMARY OF THE INVENTION

The present invention is a device and method for providing cervical traction on a patient to address or alleviate various musculo-skeletal disorders of the cervical spine or in the upper back. The device is configured to permit the patient to administer cervical traction on him or herself with minimal or no assistance in most situations. The device of the present invention is designed to be used while the patient is lying on his or her back on a substantially horizontal surface such as a bed or other elevated support. The device of the present invention includes a head rest assembly adapted to releasably contact the patient's neck proximate to the occipital region, means for exerting tension force on the head rest assembly, and a tractive force transferring system which includes a tension line connected to the head rest assembly and to the tension exerting means. The tractive force transferring system may also include a tension transferring line connected to the tension line. The tension release line terminates in means for releasably contacting an appendage of the patient, such that the patient-user can interrupt the tension force transferred to the tension line.

The head rest assembly of the present invention can include a base which can be capable of pivoting about a first leading edge which is adapted to be in sliding contact with the elevated support surface on which the patient-user lies. A pair of members are mounted on the base proximate to the first end and protrude upward therefrom. The upwardly protruding members have a height and contour sufficient to releasably contact the skull of the patient-user.

In the first embodiment of the present invention, the aforementioned elements are configured to provide cyclic traction which alternates between exertion of a traction load and complete rest. In the second embodiment of the present embodiment, the aforementioned elements are configured to provide cyclic and/or intermittent traction between a first traction force and a second traction force and include means for accomplishing this function.

The cervical traction device of the present invention may also include suitable traction load limiting devices and dampening or shock absorbing mechanisms.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

The cervical device of the present invention provides a device and method whereby controlled cervical traction force can be administered effectively in a variety of locations such as the home or physical therapist's office in an economical manner. The device can be used in a therapeutic program to apply cervical traction force in either an intermittent manner, cyclical manner or in a completely non-cyclical manner. In the cyclical mode of operation, cervical traction force is exerted, then released, over a prescribed period of time or a number of repetitions and alternates either between a first tractive force and a second lower tractive force or between a tractive force and a no-load phase. In the non-cyclical mode of operation, cervical traction force is applied in an essentially constant manner for a prescribed period of time. When tractive force is applied in the intermittent manner, as that term is applied in this application, the amount of tractive force cycles between a total tractive load or "on" position and a partial tractive load position. The ability to adjust the tractive force exerted is available in any combination of intermittent, cyclical and non-cyclical operating modes.

The ability to cycle (i.e. release or reduce tractive tension) permits the overall amount of cervical traction force exerted on the cervical region to be increased. This is particularly advantageous as therapy progresses, because the patient-user will find it necessary to employ elevated levels of tractive force to maximize therapeutic benefit. However, if tractive force is to be increased, the tractive force must be cycled rather than applied as static load to prevent injury which could occur if high levels of tractive force are exerted for prolonged periods of time. Cycling permits a patient to employ greater tractive force with minimal risk of injury.

The cervical traction device of the present invention is designed to be used with a patient in the supine position. The supine position permits relaxation of the neck muscles in order to permit optimal cervical traction effectiveness.

Figures 1, 3:
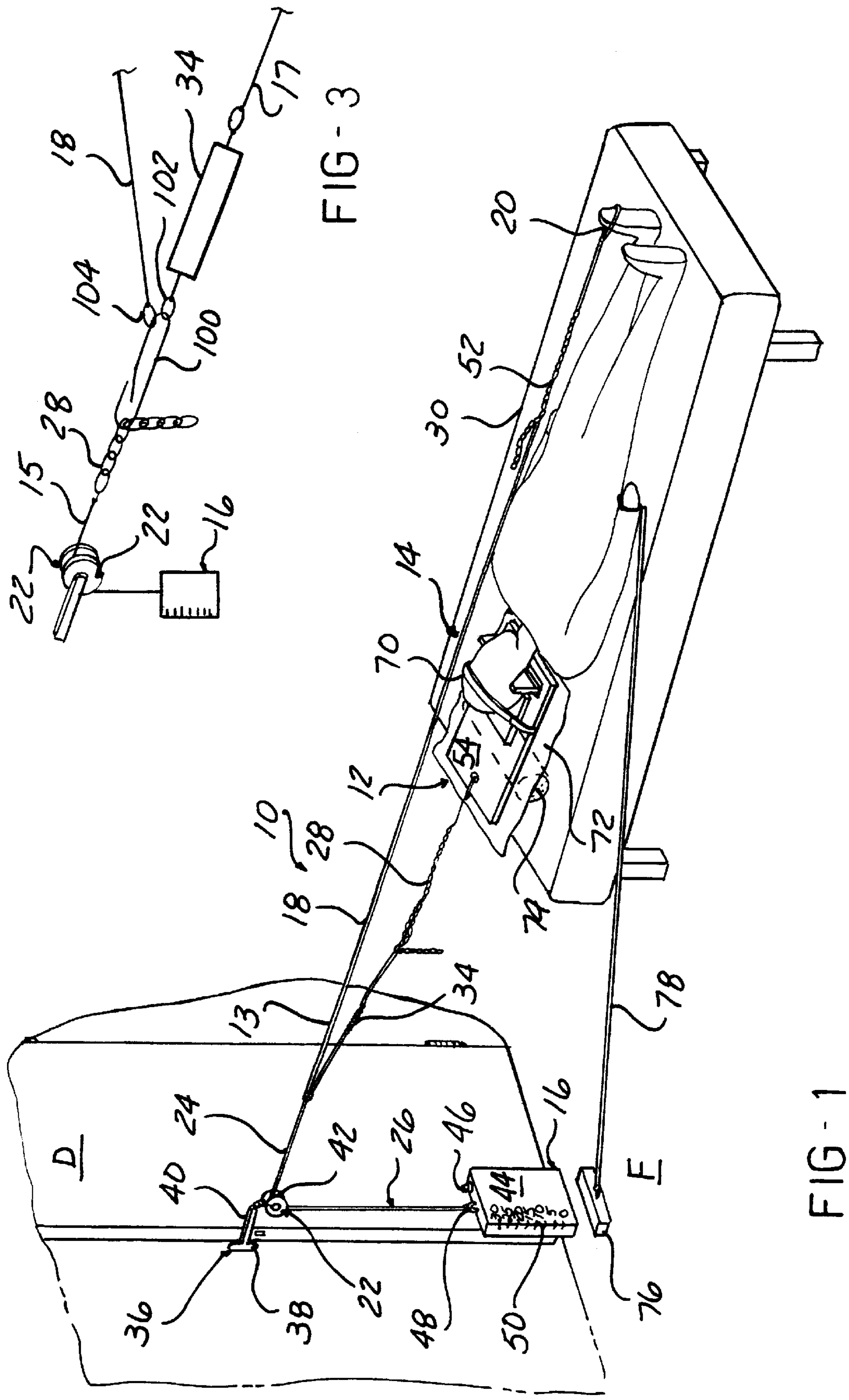
FIG. 1 is a perspective view of the first embodiment cervical traction device of the present invention, configured for cyclic application.
FIG. 3 is a detail view of the linkage of the tractive force transferring system of the first embodiment of the present invention.
Figure 4:
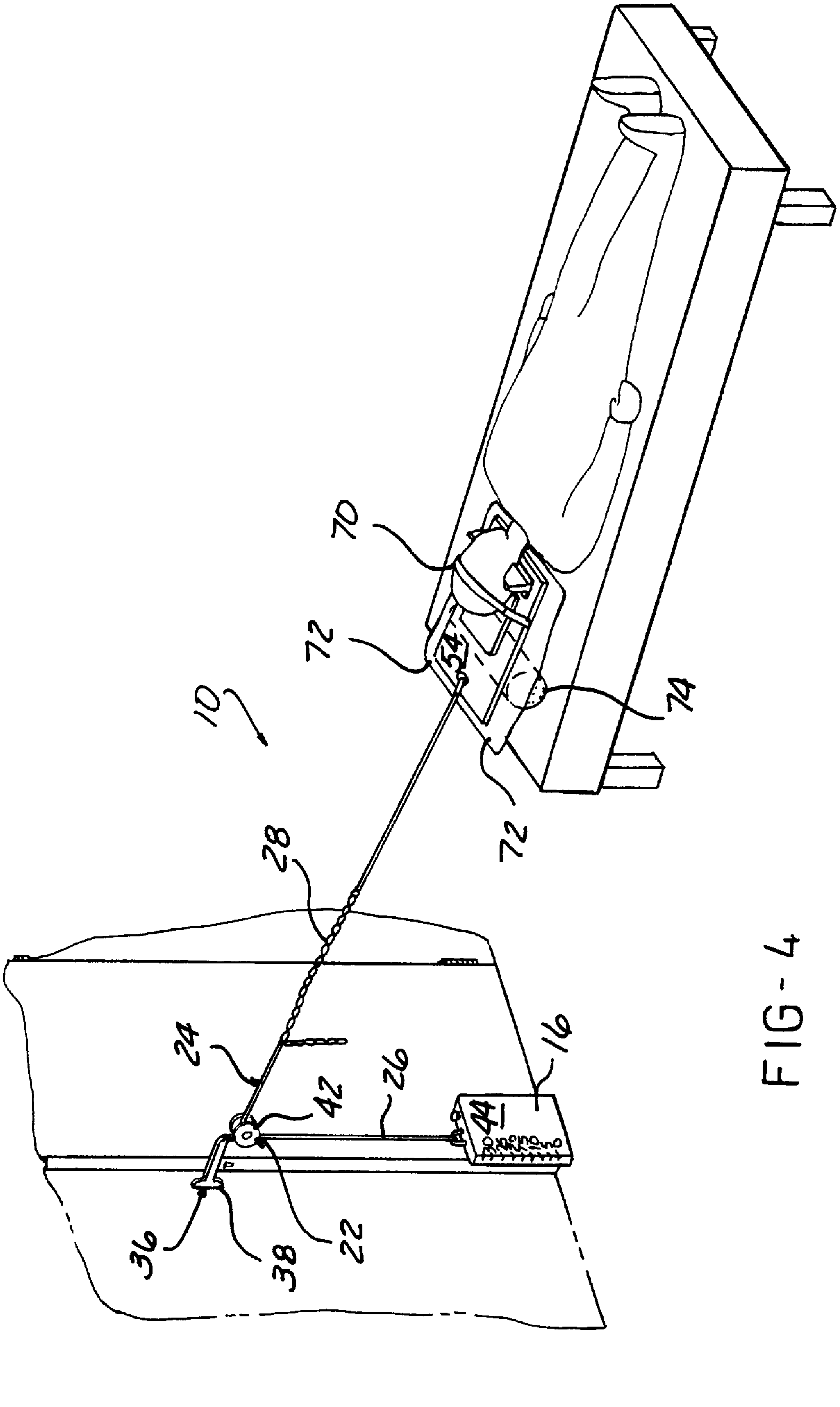
FIG. 4 is a perspective view of the first embodiment cervical traction device of the present invention configured for static cervical traction.
Figure 5A:
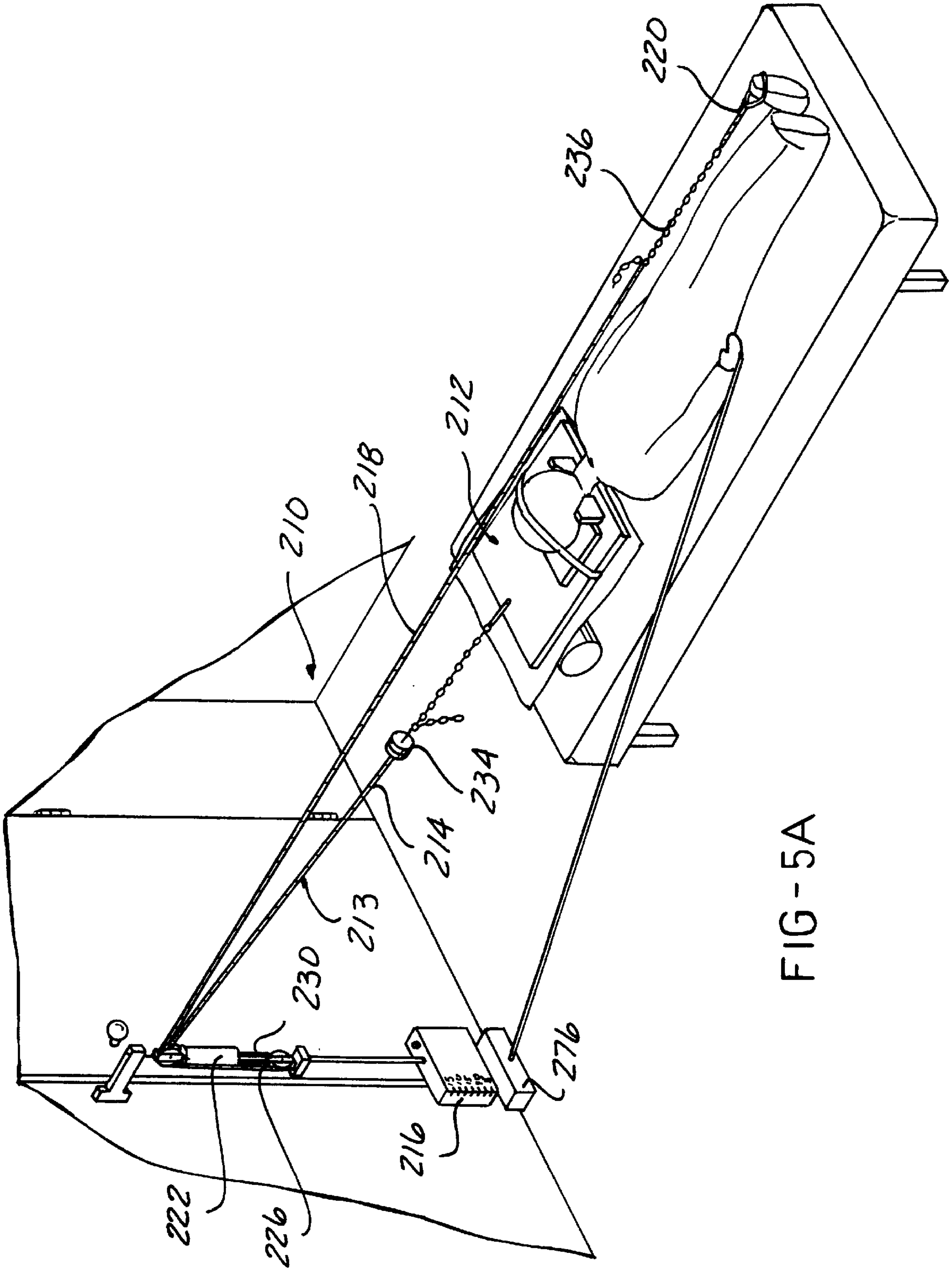
FIG. 5A is a perspective view of the second embodiment of the present invention configured for intermittent application of traction.
Figure 5B:
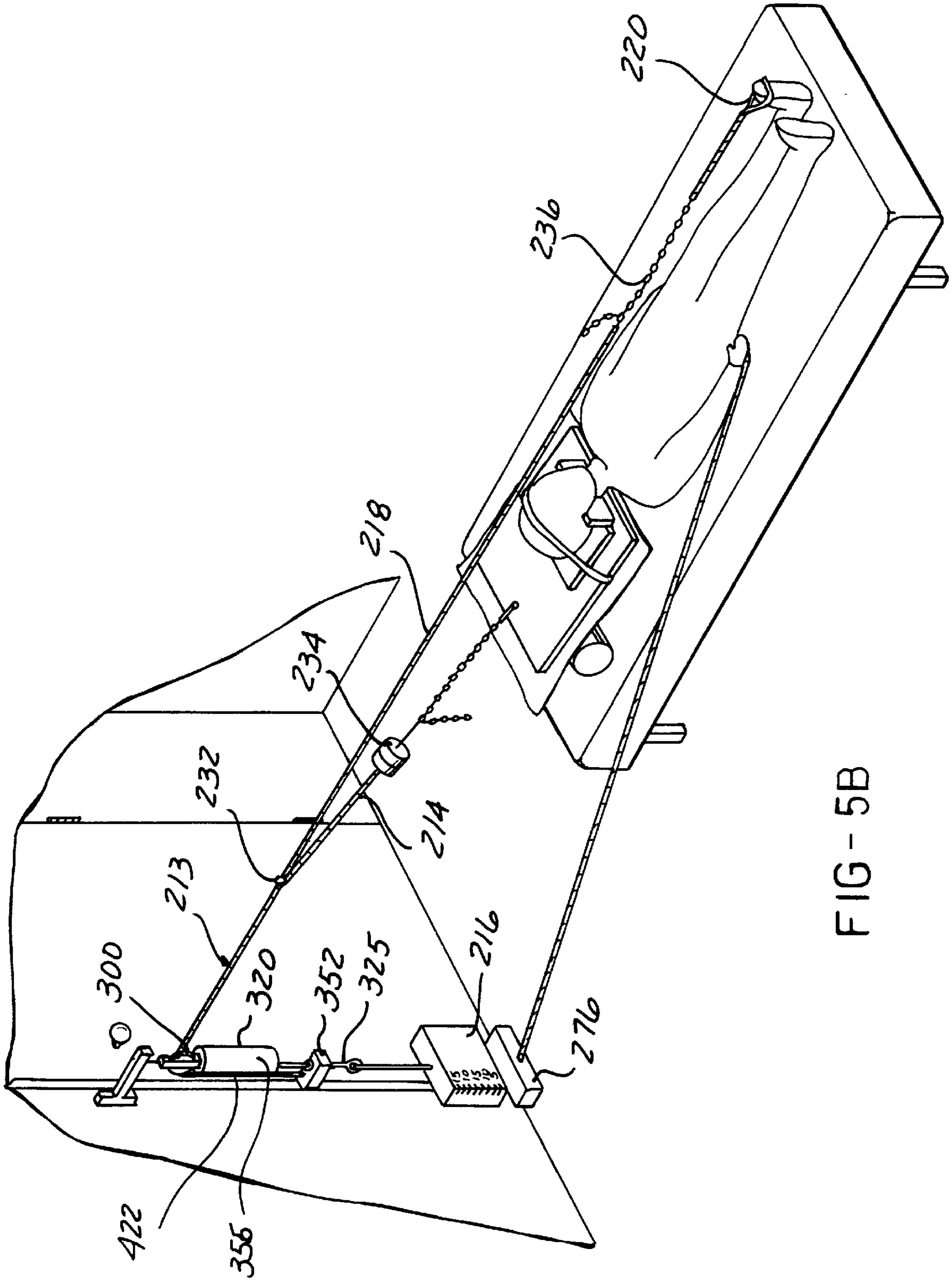
FIG. 5B is a perspective view of the second embodiment of the present embodiment configured for cyclic application traction.

In general as shown in FIGS. 1 and 5A–B, the cervical traction device 10, 210 of the present invention is composed of a head rest assembly 12, 212 to which a suitable tension transfer system 13, 213 including tension line 14, 214 is suitably attached. The tension transfer system 13, 213 is capable of transferring a tractive force from a suitable means for exerting tractive force to the head rest assembly 12, 212. When the cyclical or intermittent mode of operation is required, the tension transfer system 13, 213 of the cervical traction device 10 of the present invention also includes means for interrupting or varying the tractive force exerted on head rest assembly 12, 212. This tractive force interruption means includes a tension release line 18, 218 attached to the tension line and terminating in a means for engaging an appendage of a patient such as a loop or suitable handle device 20, 220. The embodiment shown in FIG. 4 is directed to the application of a constant level of tractive force therefore the tractive force interruption means is omitted.

In the first embodiment as set forth in FIGS. 1 and 4, the tension line 14 has a first end attached to the head rest assembly 12 and a second end attached to means for producing tractive force. As shown in FIGS. 1 and 4, this tractive force producing means is preferably weight 16 which will be discussed in greater detail subsequently.

The tractive force transferring system 13 can also include a suitable pulley mechanism such as pulley device 22. In the device of the present invention as shown in FIGS. 1 and 4, the tension line 14 extends through pulley device 22 and is moveable relative thereto. The pulley device 22 is adapted to be mounted to a suitable surface at a location elevated relative to the head rest assembly 12 such as the door D depicted in FIG. 1, or to a wall, etc. The tension line 14 passes through the pulley device 22 in a manner such that the tension line 14 is provided with a first leg 24 extending between pulley device 22 and head rest assembly 12. The tension line 14 also includes a second leg 26 extending between pulley device 22 and weight 16. The second leg 26 is essentially perpendicular to the floor.

In the cyclical version of the first embodiment as shown in FIG. 1, tension release line 18 is attached at a first end thereof to the tension line 14. Preferably, the point of attachment between the tension line 14 and the tension release line 18 is located in the first leg 24 of the tension line 14, i.e. between the point at which the tension line 14 is attached to the head rest assembly 12 and the point at which the tension line 14 passes through pulley device 22. The tension release line 18 terminates in a suitable handle device 20 which can be grasped by the user to manually relieve or release the tractive force exerted by weight 16. Preferably, the patient inserts a foot in the handle device 20 to manually release the tractive force in the manner to be described subsequently.

The tension line 14 may be equipped with a suitable means for adjusting the length of the first leg 24. Such means can include any type of adjustment device. The suitable adjustment devices can include rope sliders or other suitable mechanisms which would permit the proper adjustment of the tension line 14. The adjustment device can be located in either leg of the tension line 14. It is also possible to have adjustment devices located in both legs. As shown in FIGS. 1 and 4, the means for adjusting the length of the first leg 24 is a linear link device 28 having a plurality of serially linked circles. The linear link device 28 is, preferably, located in the first leg 24 at a position between the point of attachment to the head rest assembly 12 and the pulley device 22. As shown in FIG. 1, the linear link device 28 is composed of a plurality of serially linked oval members to form a chain linkage. Preferably, the tension line 14 is equipped with at least one clip member or other (rope slider) for removable adjustment to the appropriate link member of the chain device 30.

The tension line 14 may also include an optional safety load limiter 34 located in the tension line 14 at any convenient location between head rest assembly 12 and the weight 16. The load limiter 34 may be any suitable device which will dampen the return force transferred to the cervical region of the patient. Suitable examples include, but are not limited to, dampeners, shock absorbers, mechanical fuses and the like. Such devices can function to prevent over elevated load forces being applied. Such devices can also prevent the transfer of a sudden shock force through the traction device.

Figure 6B:
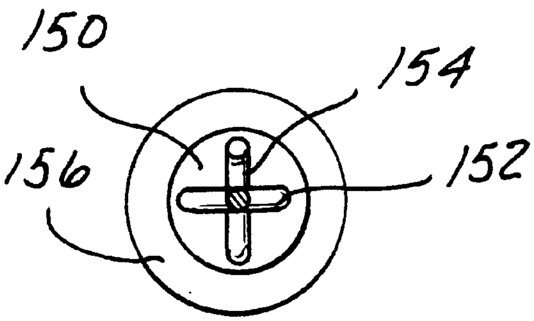
FIG. 6B is a top view of the load limiter of FIG. 6A taken along the 6B—6B line.
Figure 6A:
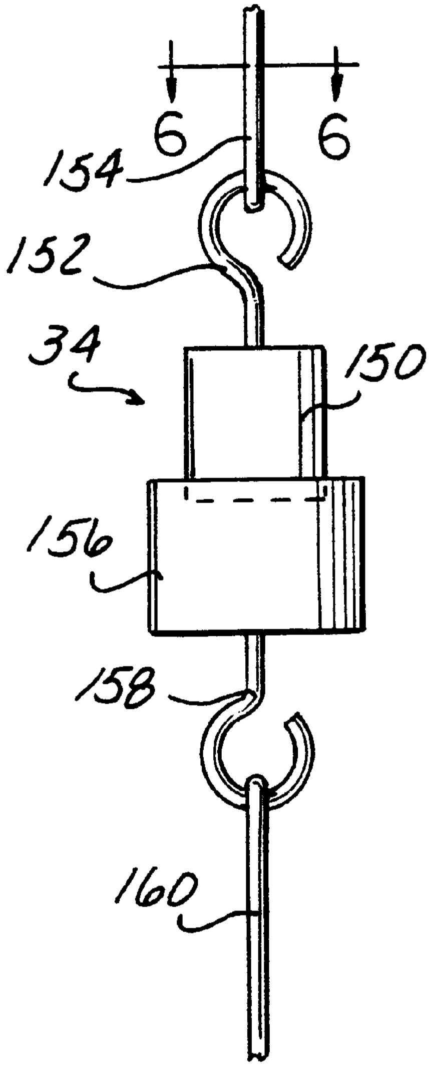
FIG. 6A is a detail side view of a load limiter device suitable for use with the cervical traction device of the present invention.
Figure 6C:
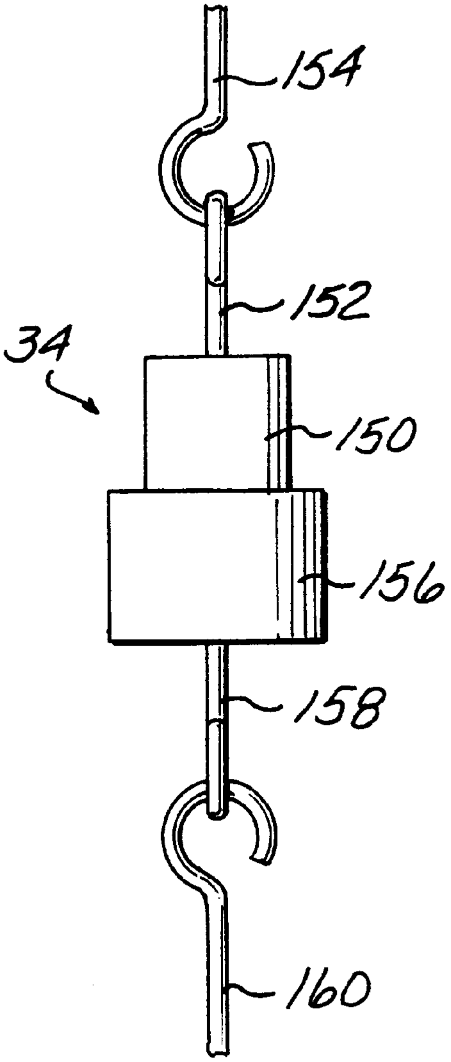
FIG. 6C is a side view of the load limiter of FIG. 6A.

One preferred type of load limiter is the weight limiter shown in detail in FIGS. 6A, 6B, and 6C. Such device includes a magnet 150 having a defined rated holding value. A suitable attachment mechanism such as hook 152 is connected to magnet 150 such as by threaded insertion therein or the like. The first portion tension line 14 is attached to hook 152 by suitable eye member 154. The magnet 150 releasably engages a metallic mating member 156 which, in turn, also includes a suitable attachment mechanism such as hook 158 connected thereto by any suitable means such as threaded fastening therein. The second portion of tension line 14 is connected to eye member 160. The rated holding value of magnet 150 to separate from the metallic mating member 156 in the event that a load greater than the rated holding valve of the magnet is exerted through tension line 14. Thus, if load occurs for any reason which exceeds that rated holding valve of the magnet 150 or the unit is loaded beyond its rated value, the metallic mating member 156 will separate preventing transfer of the excess load to the head rest assembly 12. The magnet 150 also limits the weight a patient can use to exert tractive force. Thus, appropriate tractive force cannot be exceeded.

The load limiter 34 may be positioned at any location which will accomplish the necessary protection of the patient from experiencing an excessive load force. As shown in FIG. 1, a load limiter 34, such as a mechanical fuse is located between the point of attachment of the tension line 14 to head rest assembly 12 and the point of attachment of tension release line 18 to tension line 14. When employed in combination with a length adjustment device such as the linear link device 28, it is preferable that the safety shock force protector 34 be positioned between the adjustment device and the point of attachment of tension release line 18. In situations where a magnetic load limiter 34 such as that illustrated in FIGS. 6A, 6B, and 6C is employed, it is desirable to position the load limiter 34 in leg 26 of the tension line 14. However, it is understood that other load limiters such as gas cylinders can also be employed to dampen or absorb a portion of the tractive force exerted. Examples of such devices deployed in the device of the present invention will be described subsequently.

As shown in detail in FIG. 3, the tractive force transferring system 13 of the first embodiment of the present invention can be configured so as to have a central clip member 100 to which a suitable loop 102 in the tension line 14 and a loop 104 in tension release line 18 may be fastened. In order to adjust the length of tension line 14 the linear linked device 28 may be positioned so as to engage the central clip member 100 in an adjustable manner as depicted in FIG. 3. One end of the linear linked device 28 is connected to a first length of suitable rope or line 15 to which a suitable weight or other tension producing means 16 is attached at the opposite end. When the length adjustment system depicted in FIG. 3 is employed load limiter 34 functioning as a, the safety shock force protector can also be attached to the clip member 100. In such situations, the optional load limiter 34 is attached to an eyelet 102 and a second length of suitable rope or line 17 which is, in turn, attached to the head rest assembly 12. The optional tension release line 18 is also configured to be suitably attached to clip member 100 to effect attachment of the tension release line 18 to the tension line 14.

As depicted in FIG. 1, the tractive force transferring system 13 of the cervical traction device 10 of the first embodiment of the present invention includes pulley device 22. The pulley device 22 can be mounted to any suitable surface either permanently or in a removable fashion. As depicted in FIG. 1, the pulley device 22 is mounted to door (D). It is within the purview of this invention that the cervical traction device 10 be mounted to any suitable element which will support the appropriate weight. This can include, but is not limited to doors, walls, and suitable stands. Preferably, the pulley device 22 includes a mounting support 36 to which the pulley is flexibly attached. The mounting support 36 can either be permanently attachable to a suitable vertical device such as door (D) by means of appropriate set screws or the like or can be removably mounted as is shown in FIG. 1. Where the mounting support 36 is configured to be removably mounted to a door, the mounting support 36 includes a first planar device adapted to be positioned in abutting parallel relationship to the end of door (D) and a contiguously mounted perpendicular second planar member 40 adapted to be positioned in abutting relationship to the door surface opposed to the location of the cervical traction device 10.

In order to maintain the mounting support 36 in position on the door (D), the mounting support 36 is, preferably, located above the door knob and bolt mechanism. The door (D) is closed thereby providing a secure mount which is exposed to minimal vertical or horizontal shifting. Alternately, the mounting support 36 could be mounted above a suitable door hinge.

The pulley device 22 may include a single pulley or a plurality of pulleys suitable for transferring tension to the head rest assembly 12. In the first embodiment, a single pulley is employed to ensure that maximum cervical traction force is transferred to the head rest assembly 12.

The pulley device 22 is mounted at a height equal to or greater than the height of the head rest assembly 12 above the floor F. In the first embodiment, the pulley device is mounted such that the angle between the first and the second legs is less than 90°. It has been found that at such an angle, cervical traction force is most expeditiously transferred to the head rest assembly 12 to be imparted to the patient in the manner to be described subsequently.

In the first embodiment of the cervical traction device of the present invention, cervical traction force may be imparted by any suitable means for exerting cervical traction force such as weight 16. When a weight such as weight 16 is used, it is suspended from the terminal end of the second leg 26 of the tension line 14.

As shown in FIG. 1, the weight 16 can be a suitable container device 44 having an opening 46 to permit access to the interior of the container device 44. The container device 44 also includes suitable means for attachment to the terminal end of tension line 14. As shown in FIG. 1, such attachment means can be a built-in hook 48. The container device 44 can also include a series of graduated markings 50 located on the exterior surface calibrated to correspond to weight values when the container device 44 is filled with the appropriate amount of a selected fluid material. The fluid material can be any pourable material such as sand, water and the like. Preferably, the fluid material employed in the container device 44 of the present invention is water. It has been found that using water as the weight medium permits easy handling and manipulation by the patient, is readily available, and can be easily disposed of as necessary. The amount of water or other fluid material to be added to the container device 44 is determined by the needs of the individual patient. The amount of cervical traction force to be imparted will vary from patient to patient depending upon the therapy protocol and rehabilitation needs of the patient. Thus, the total weight can be varied accordingly. It is also contemplated that it may be desirable to vary the amount of cervical traction force during the course of an individual's physical therapy treatment. Thus, the container device 44 of the present invention permits great flexibility in tailoring the cervical traction force to the needs of the patient.

The tractive force transfer system employed in the cervical traction device 10, 210 of the present invention may include a tension release line 18 by which the patient in cervical traction can cycle the amount of cervical traction force being applied. As indicated previously, the tension release line is attached to the tension line 14 at a point between the pulley device 22 and the point of attachment to the head rest assembly 12. The tension release line terminates in a suitable handle device 20 into which the user of the cervical traction device 10 can insert his or her hand or foot. Extension of the arm or leg results in the release of tractive force exerted on the head rest assembly 12. Bending and flexing of the arm or leg results in the transfer of tractive force to the head rest assembly 12. The tension release line 18 can also include a suitable means for adjusting the length of line 18 such as linear linked device 30. In this manner, the cervical traction device 10 can be modified to adapt to patients of varying heights. The length adjustment device can be any suitable linear adjustment means such as a rope slider (not shown) or a linear link device such as link device 52.

Figure 2:
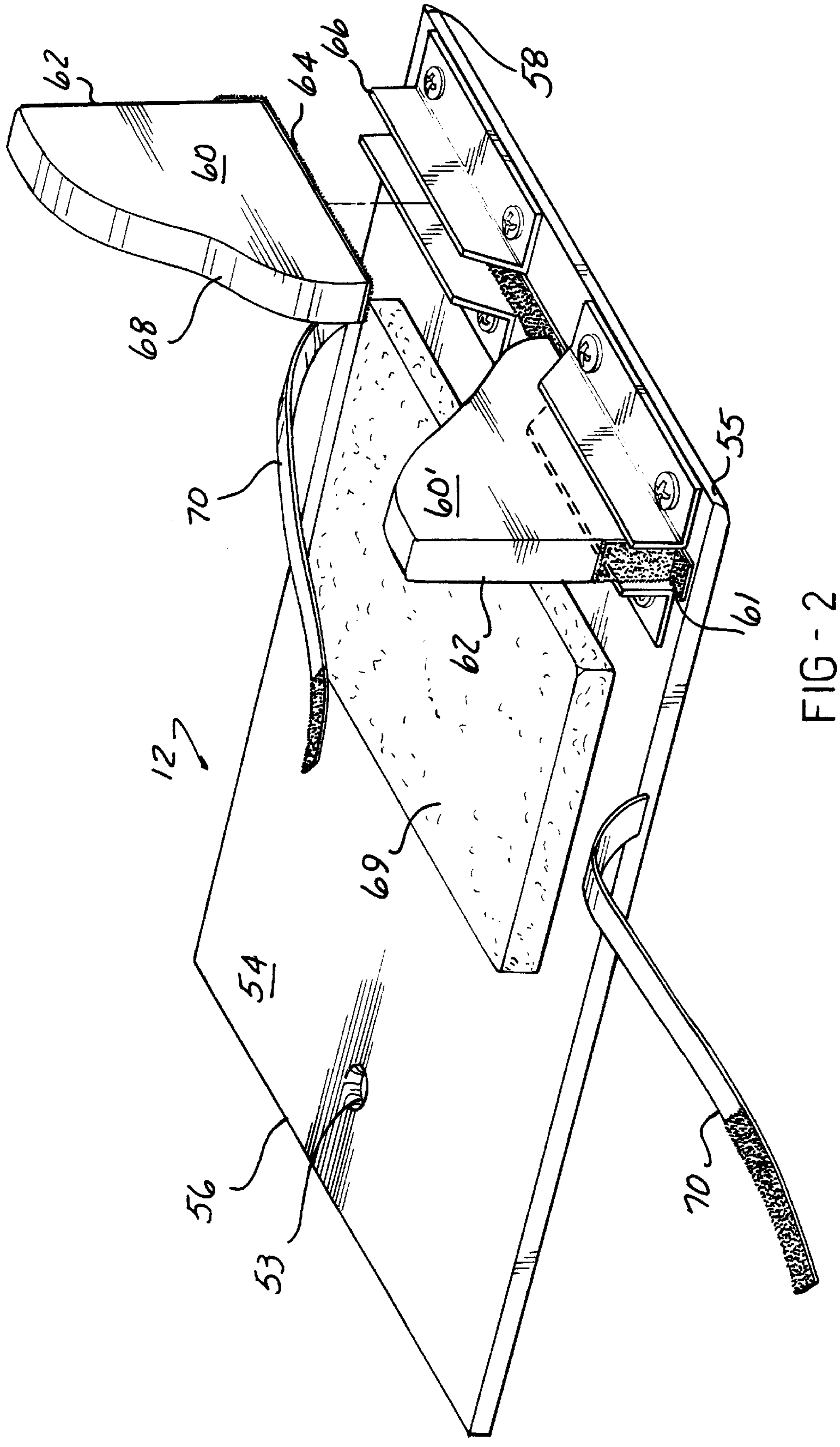
FIG. 2 is a detail perspective view of one alternate embodiment of the head rest assembly of the present invention.

The head rest assembly 12 of the present invention is shown generally in FIG. 2. The head rest assembly 12 is generally composed of a base 54 having a first end 56 and an opposed second end 58. Means for attachment of the first end of the tension line 14 are located proximate to the second end 58 of the base 54 of the head rest assembly 12. As shown in FIGS. 2 and 12, the attachment means is preferably an aperture through which the first end of the tension line can be inserted and attached.

The first end 56 of the base 54 of the head rest assembly 12 has a forward edge 55 which is geometrically configured and adapted to facilitate pivoting along the edge surface and provide ease of sliding during the application of tractive force. The forward edge 55 may be configured as a curved radius as shown in FIG. 1, a partial radius, or a suitable geometry to facilitate sliding movement.

The base 54 of the head rest assembly 12 also includes adjustable means for releasably engaging the skull of the patient in the region proximate to the patient's neck. Preferably, engagement occurs in the occipital region located at the rear base of the skull immediately above the cervical spinal region of the neck. In the preferred embodiment, the patient engagement means are a pair of upwardly protruding members 60, 60' adjustably mounted proximate to the first end 56 of the base 54 of the head rest assembly 12 and protruding approximately perpendicularly therefrom.

The upwardly protruding members 60, 60' can be mounted to the head rest assembly 12 in any manner which would facilitate the lateral adjustment of the two members relative to each other to receive the lower rear region of the respective skulls of various patient-users. As depicted in FIG. 2, each upwardly protruding member 60, 60' has a sidewardly edge 62 adapted to extend upward from the upper surface of the base 54 of the head rest assembly 12 and a contiguous edge 64 adapted to contact the upper surface of the base 54 of the head rest assembly 12 in a laterally adjustable manner. The contiguous edge is received within a suitable channel 66 which provides sufficient mechanical connection between the base 54 of the head rest assembly 12 and the given upwardly protruding member 60, 60' to prevent movement of the member 60, 60' during use of the cervical traction device 10. To further anchor the upwardly protruding members 60, 60' relative to one another, the contiguous edge 64 and the corresponding region of the upper surface of the base 54 of the head rest assembly 12 can have a suitable loop-and-eye type of fastener 61 such as a VELCRO-type mounted thereto.

The orientation of the loop-and-eye fastener material 61 and the channel 66 with respect to the contiguous edge 64 of the respective members 60, 60' permits great latitude in the adjustable positioning of the upwardly protruding members 60, 60' relative to one another. The two members 60, 60' can be positively positioned in the channel 66 to meet the needs of the individual use and conform to the contours of the user's skull.

The upwardly protruding members 60, 60' may be configured to include a contoured region 68 extending between the terminal edges of the flat upwardly protruding edge 62 and the contiguous edge 64. The contoured region 68 includes an internally concave section located approximately medial between the two respective edges 62, 64 adapted to correspond to the contours of the skull of the patient-user. If desired, the contoured region 68 may have padding to increase user comfort during use. The base 54 of the head rest assembly 12 and the upwardly protruding members 60, 60' can be made of any suitable material. In the preferred embodiment, the base 54 of the head rest assembly 12 and the upwardly protruding members may be constructed from suitable plastic or wood materials.

As shown particularly in FIG. 2, the head rest assembly 12 of the cervical traction device 10 of the present invention can also include a skull receiving region 69 located in the upper face of the base 54 of the head rest assembly 12. Preferably, the skull receiving region 69 can be a cushioned portion mounted on the base 54 of the head rest assembly 12 to cushion any impact between the skull and the surface of the base 54 of the head rest assembly 12 during cyclical cervical traction treatment and to increase general user comfort.

The head rest assembly 12 also may optionally include forehead restraint 70 which can be employed to maintain the head of the patient-user in proper orientation during use of the cervical traction device 10 of the present invention. As shown in FIG. 2, the forehead restraint 70 is composed of two members which can be releasably joined to one another using a suitable fastening means such as a VELCRO-type fastener. The forehead restraint 70 is mounted to the sides of the base 54 of the head rest assembly 12 at a position between the first end 56 and the second end 58 which would permit fastening of the forehead restraint by the patient-user.

In the embodiment depicted in FIGS. 1 and 2, in order to transfer maximum tractive force from the tension line 14 through the head rest assembly 12 to the skull and spine of the patient-user, the cervical traction device 10 may also include a suitable friction reduction member interposed between the lower surface of the head rest assembly 12 and the surface on which the cervical traction device 10 and the patient-user is lying, for example, bed B and the bolster shown in FIG. 1. As depicted in FIG. 1, the friction reduction device may be a separate sheet 72 positioned between the lower surface of the base 54 of the head rest assembly 12. Suitable friction-reducing materials include but are not limited to chlorofluorocarbon materials such as TEFLON-type materials, various other lubricous plastics, waxed paper products and the like. The friction reduction device employed in the present invention may have any suitable configuration capable of providing friction reduced movement between the elevated support surface and the head rest assembly 12. As depicted in FIG. 1, the friction reduction device may be a separate sheet 72 positioned between the lower surface of the base 54 The separate sheet 72 may be made of one or more layers which can slide on one another, with two layers being preferred. Alternately, the friction reduction device can be attached to or formed integral with the lower face of the base of the head rest assembly 12.

In order to obtain proper angular orientation between the base 54 and the spine of the patient-user, in the first embodiment of the invention as depicted in FIGS. 1, 2, 3 and 4 the cervical traction device 10 of the present invention can also include a suitable bolster 74. The bolster 74 can have any suitable configuration which will permit the head rest assembly 12 to be maintained at an angular orientation between 0 and 40° from horizontal with an angle between about 0 and about 25° being preferred. The bolster 74 can have a cylindrical form such as shown in FIGS. 1 and 2. Positioning the bolster 74 proximate to or distant from the first end of the base 54 of the head rest assembly 12 will vary the angular orientation of the base of the head rest assembly 12. The bolster 74 can be any suitably configured device such as a pillow, towel, etc., which can be placed between the flat surface on which the patient-user lies during treatment and the lower face of the head rest assembly 12. Alternately, the bolster device can be integrated into the head rest assembly 12 to form a unitary member.

In using the cervical traction device 10 of the first embodiment of the present invention, the pulley device 22 is mounted to a suitable vertical support such as door D shown in FIG. 1. The tension line 14 is inserted through the pulley device 22 and adjusted for suitable length using the length adjustment mechanism such as linear linked device 28. Similarly, the length for tension release line 18 is adjusted to the needs of the patient-user using a length adjustment mechanism such as linear linked device 30. The upwardly protruding members 60, 60' of the head rest assembly 12 are adjusted to accommodate the skull of the patient-user and a suitable amount of weight is attached to the second end of tension line 14 to provide tractive force. The amount of weight employed is generally an amount sufficient to be tolerated by the patient-user and-to effectively provide an extension of the vertebrae in the neck and upper back region. It is to be understood that the amount of weight employed will vary from user to user depending on the nature of the injury and the general physical condition of the individual patient-user. It is also to be understood that the amount of weight employed for tractive force can vary during the course of treatment for a given individual due to changes in overall physical condition and in the healing experienced. The specific amount of weight is that which would be recommended by the physical therapist, physician or other health care professional.

When the cervical traction device 10 of the present invention is in position, the patient-user positions himself in the unit and begins cervical traction therapy. At the outset of each treatment session, it is desirable that there be no tractive force transferred through the tractive force transferring system 13 to the head rest assembly 12 to permit the patient-user the opportunity to obtain the proper position in the unit. This can be accomplished in one of three ways: the weight can be held by a third party until the patient-user indicates that he is ready to commence cervical traction treatment; the patient-user can maintain force on the tension release line 18 with a foot or other appendage; or the weight 16 can be mounted on a block member 76 as is shown in FIG. 1. When the block member 76 is employed with the cervical traction device 10 of the present invention, it is connected to a line 78 running to the location of the patient-user. The block 76 has a height sufficient to permit weight 16 to be freely suspended when the block is removed from contact with the weight. Once the patient-user is in position relative to the cervical traction device 10, tugging on the line 78 causes removal of the block 76 from contact with the weight 16 to initiate tractive force. A more preferred approach for entering the device of the present invention is to engage and apply force to line 18 with the proper appendage. Once this is accomplished, the patient-user has the option of pulling on line 18 to remove the force exerted on the head or to reach behind and above his head to pull the head rest assembly 12 into position with his hands. It is to be understood that this second option would minimize the need for line 78 and could be highly advantageous for certain types of injuries and conditions.

Also included in this invention is a second embodiment of the cervical traction device suitable for intermittently and/or cyclically administering differing levels of traction force to the cervical neck region of a patient. The cervical traction device 210 of the second embodiment as set forth in FIGS. 5A and 5B includes a head rest assembly 212 to which a suitable tension transfer system 213 including tension line 214 is suitably attached. The tension transfer system 213 is capable of transferring tractive force from a suitable means 216 for exerting tractive force to the head rest assembly 212. The tension transfer system 213 also includes means for varying the tractive force exerted on head rest assembly 212. The tractive force varying means includes tension release line 218 attached to tension line 214 at one end and terminating at a second end in a suitable means for engaging an appendage of a patient such as a loop or suitable handle device 220.

In the second embodiment set forth in FIGS. 5A and 5B, the tension line 214 is attached at one end to the head rest assembly 212 and provides connection between the head rest assembly 212 and the means 216 for producing tractive force. The means for producing tractive force may be any suitable mechanism such as weight 216 described previously in connection with FIG. 1.

The tractive force transferring system 213 can also include suitable pulley mechanisms for directing the various lines and redirecting tractive force as required. In the second embodiment as shown in FIG. 5A, the cervical traction device 210 includes a double pulley device 222 through which tension line 214 passes defining a first region of the tractive force transferring system 213. The double pulley device 222 is adapted to be mounted to a suitable support surface such as door D depicted in FIG. 5A or to another suitable support surface such as a wall, stand, etc.

Figure 7:
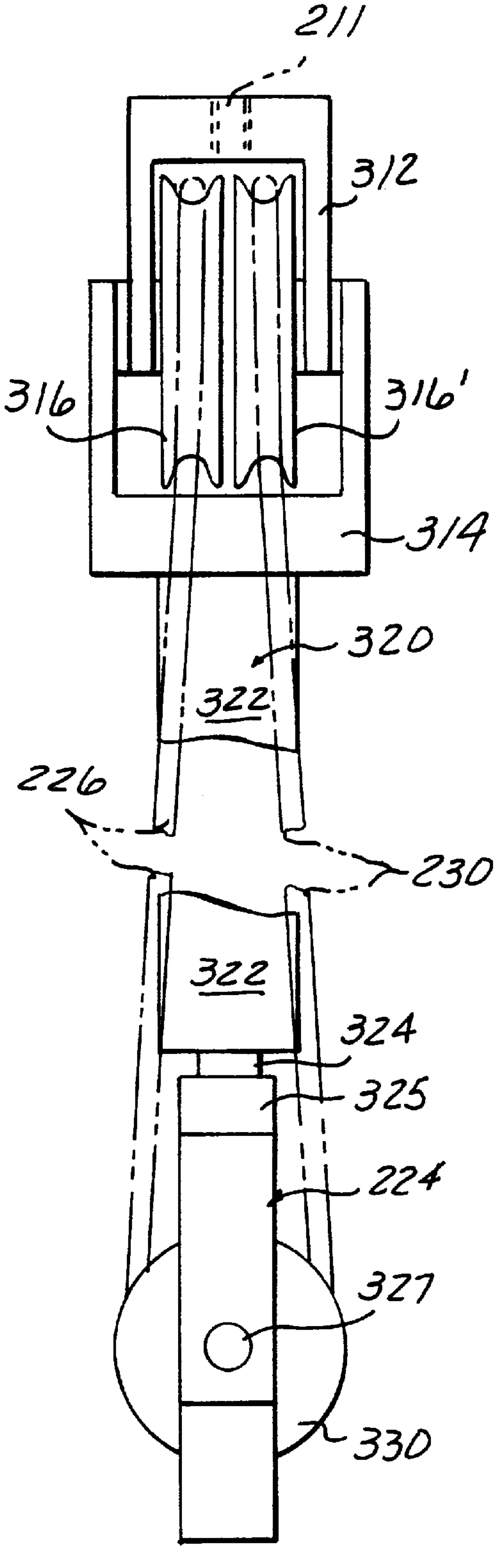
FIG. 7 is a detail view of an alternate pulley arrangement for use with the second embodiment of the present invention including an alternative dampening system.
Figure 8:
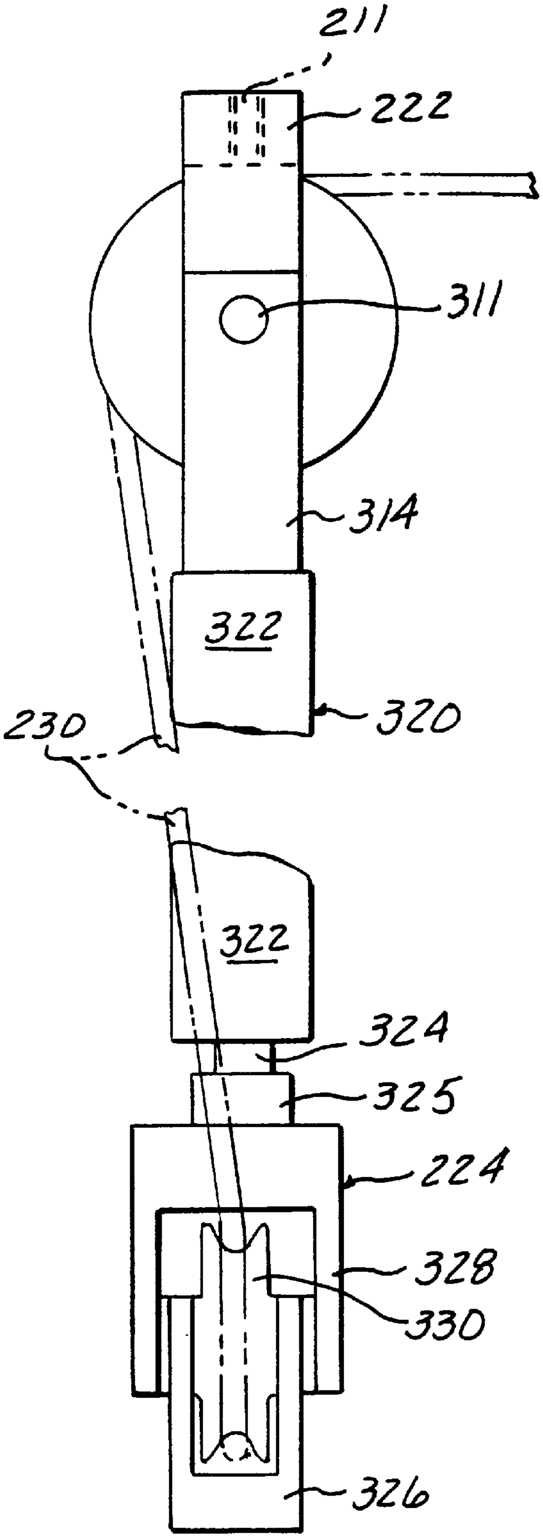
FIG. 8 is a side view of the alternate pulley arrangement of FIG. 7.

The double pulley device 222 is depicted in detail in FIGS. 7 and 8. The device includes an inner clevis 312 matingly received with an outer clevis 314. Two pulley members 316, 316' are rotatably mounted on a rod 311 within the inner clevis 312. The inner clevis 312 includes suitable means for attaching the double pulley device 222 to the mounting means 211 such as attachment aperture into which mounting means can be threadingly attached.

A suitable shock prevention load dampening device such as dampening means 320 can be attached to the outer clevis 314 either directly, by thread engagement by a suitable length of rope or other suitable device. The dampening means 320 is, preferably, a dampening cylinder having an outer housing 322 and an inner rod 324 telescopically received therein. Suitable dampening cylinders can be configured using gas springs or the like. Preferably, the dampening device employed is one which is capable of dampening loads up to approximately 50 pounds over a period of 5 to 10 seconds.

A single pulley unit 224 is attached to the outwardly projecting end of inner rod 324. As shown in FIG. 8, the single pulley unit 224 includes an inner clevis 326 received within an outer clevis 328. A single pulley member 330 is rotatably mounted on a rod 327 extending through the central region defined by inner clevis 326 and outer clevis 328. The outwardly projecting end of inner rod 324 is attached to the outer clevis 326 by any suitable means such as threading insertion into a suitable aperture defined in the outer clevis 328, (not shown) welding or the like to permit movement of the single pulley unit 224 moves with the telescopic movement of the inner rod 324 relative to the outer housing 322 of dampening cylinder.

As depicted in FIGS. 7 and 8, inner clevis device 326 is connected to a tractive force producing means 216 by any suitable attachment means. It is preferred that attachment include a suitable eye or other device (not shown) inserted into an aperture prepared in inner clevis 326 (not shown). The eye or other hook device can attach to a mating hook attached to tractive force producing means 216 either directly or through a suitable length of rope.

Upon passing through double pulley device 222, tension line 214 is redirected and forms a second leg defined at one end by double pulley device 222 and at the opposed end by single pulley device 224. Preferably, a load limiter 234 such as that previously described in detail in relation to FIGS. 6A, 6B, and 6C is included in the tension line. The weight limiter 234 can be located in the tension line 214 at any suitable position between the headrest and the weight.

Tension line 214 also includes a stop member 226 in leg B which, when engaged between pulley 224 and clevis 326, allows the force created by weight 216 to be totally transferred to tension line 214.

As employed in FIG. 5A, the tension line 214 passes through single pulley device 224 and on to double pulley device 222 defining a leg of the tension line 214. Located in this leg is stop member 230 which, when engaged between pulley 330 and clevis 326, allows the weight 216 to be lifted by the tension release line 218. Travel of single pulley device 224 relative to the tension line 214 is limited thereby. This permits total removal of load exerted on patient's cervical region. In this second embodiment, tension release line 218 is integrally joined to the leg of tension transfer line 214. Thus, in the second embodiment, one line can be employed for both the tension transfer functions and tension release functions by virtue of the pulley arrangement and stop members described.

The device of this embodiment also includes a bushing 325 or other suitable means for providing a fully dampened stroke of the gas spring during tension. As shown in FIGS. 7 and 8, a suitable bushing 325 is positioned annularly around inner rod 324 of gas cylinder 322 to limit upward travel. The bushing 325 may be constructed of suitable resilient material such as nylon. The shock load prevention/load rate controlling mechanism employed in the traction device will give the patient safe traction and a controlled rate of return of the tractive force on the neck. This controlled rate is repeated during each cycle.

The tension release line portion 218, preferably includes suitable means 232 for adjustment of the length of the tension transfer line 218 such as a tension adjustment clip, rope slider, or linear link device. In the embodiment shown in FIGS. 5A and 5B, the tension adjustment line includes a linear link device 236 to which foot loop 220 is also connected.

The traction device of the present invention can also be configured in the manner depicted in FIG. 5B to provide cyclic application of traction. As depicted in FIG. 5B, the traction device includes pulley device 422, shown in greater detail in FIGS. 9 and 10. As shown in detail in FIGS. 9 and 10, the pulley device 422 includes an inner clevis 312 matingly received with an outer clevis 314. A single pulley members 350 is rotatably mounted on a rod 311 within the inner clevis 312. The inner clevis 312 includes suitable means for attaching the pulley device 422 to the mounting means 211 such as attachment aperture into which mounting means can be threadingly attached.

A suitable shock prevention load dampening device such as dampening means 320 can be attached to the outer clevis 314 either directly, by thread engagement by a suitable length of rope or other suitable device. The dampening means 320 is, preferably, a dampening cylinder having an outer housing 322 and an inner rod 354 telescopically received therein. Suitable dampening cylinders can be configured using gas springs or the like. Preferably, the dampening device employed is one which is capable of dampening loads up to approximately 50 pounds over a period of 5 to 10 seconds.

A suitable mounting block 352 is attached to the distal end of inner rod 354. Also attached to this block is the terminal end of tension line 214. Suitable weight 216 is connected to the block 352 by any suitable means such as eyelet pin 325 shown in FIG. 5B.

Figure 9:
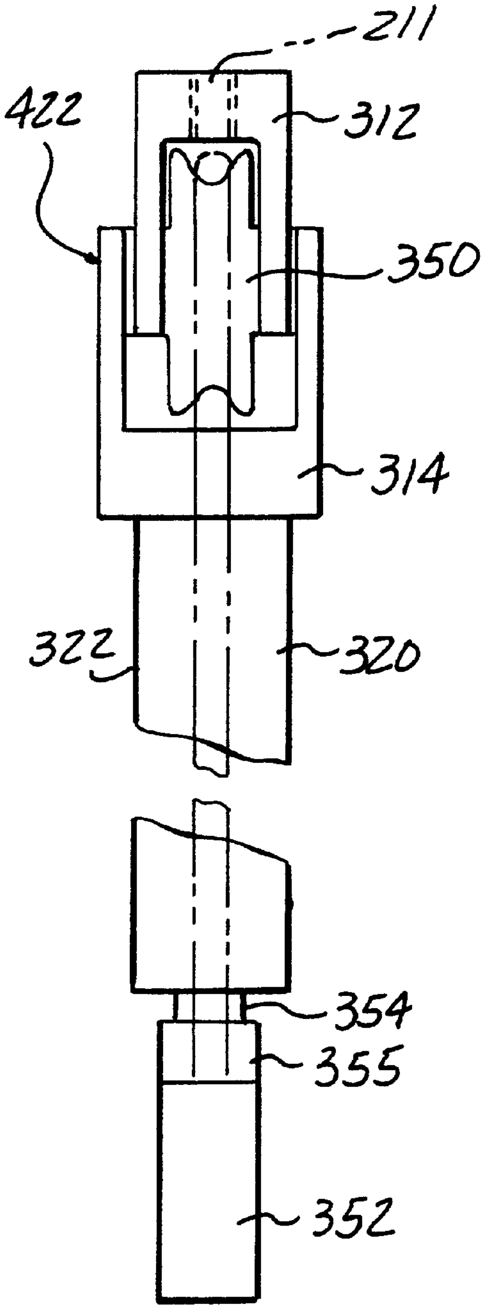
FIG. 9 is a detail view of an alternate pulley arrangement for use with the first embodiment of the present invention including an alternative dampening system.
Figure 10:
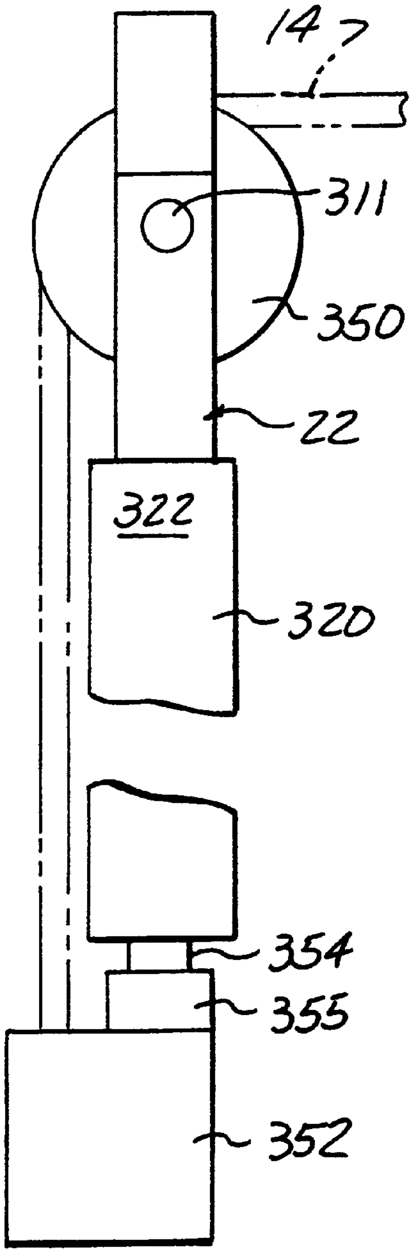
FIG. 10 is a side view of the alternate pulley arrangement of FIG. 9.

Load limiter protection can also be employed in a static load embodiment of the present invention. One suitable configuration for the load limiter protector means is shown in FIGS. 9 and 10 as a force dampener mechanism. Where a dampener such as dampener 320 is employed in a cycling embodiment, a single pulley unit 22 is employed with the gas cylinder attached thereto. Tension line 14 passes over pulley member 350 and terminates at bottom of block 352 to which weight 216 is connected. Block 352 is also connected to the distal end of internally telescoping member 354. When pressure is exerted on tension release line 18, the block 352 is drawn upward allowing telescoping member 354 to retract into outer housing 322. When the tension on tension release line 18 is released, the telescoping member 354 slowly extends due to the pressure exerted by weight 216 until the full load is transferred to tension line 14. The slowed motion is a result of action dampening device 320 which allows no restriction of motion when contracted or compressed and restricts motion during extension.

In order to provide a fully dampened stroke of the gas spring during tension, the dampener 320 includes means for providing a fully dampened stroke of the gas spring during tension. As shown in FIGS. 9 and 10, a suitable bushing 355 is positioned annularly around inner rod 324 of gas cylinder 356 to limit upward travel of block 352 as the rod 354 is retracted into cylinder 356. The bushing may be constructed of suitable resilient material such as nylon.

Thus in the second embodiment of the cervical traction device of the present invention when foot loop 218 extension begins, half of the force imparted by weight 216 is transferred to the foot and half of the force remains on the neck due to the pulley configuration. Thus, tractive force imparted on the cervical region of the neck is one half the total weight of weight 216. When the foot is further extended, stop 226 engages between pulley 330 and clevis 326. This transfers the total force imparted by the weight 216 to the foot loop and takes all the weight off of the patient's neck. This allows the patient the option of intermittent or cyclic traction. Thus, the cervical traction device of the second embodiment provides a system whereby a patient can receive tractive force which alternates between full load and a portion of that amount (intermittent) or full load to no load (cyclic).

The method for administering physical therapy using the device of the present invention in the cycling mode will now be described. Once the patient-user is in position in the device 10 of the present invention, the tractive force is applied to the neck region for an interval sufficient to provide therapeutic tractive force to the affected region. The patient-user's leg or arm will be bent or flexed so that the tension release line is not carrying the tractive force. While this interval is patient-specific, it is generally understood that this interval will be an interval sufficient to provide cervical extension without injury to surrounding tissue, i.e., less than 30 minutes. At the end of this interval, the patient-user extends the leg or arm to which the tension release line is attached thereby transferring the tractive force from the head rest assembly 12, 212 and the neck region to initiate a rest interval. The rest interval is generally a period sufficient to provide relaxation of the affected region. Without being bound to any theory, it is believed that an interval of less than one minute with an interval of about 10 seconds being preferred will be effective in many instances. At the end of the rest interval, the patient bends the leg thereby transferring tractive force back to the tension line 14, 214 through head rest assembly 12, 212 to the neck region. Abrupt jolts which could occur as a result of a sudden release in the tension line 14, 214 are eliminated due to the presence of dampener 320.

The cycle of cervical traction and rest is repeated for a period prescribed by the patient's physician, physical therapist or other health care giver. The interval can be defined by elapsed time or cycle repetitions as desired and tolerated by the individual patient-user. In order to time the cycles, a suitable visual or auditory timing device can be employed with the cervical traction device 10 of the present invention to assist the patient-user in maintaining the proper intervals of rest and cervical traction. Suitable devices could be but are not limited to electronic timers, mechanical timers, auditory tapes with appropriate timing signals and the like.

The cyclical repetition of alternating rest and cervical traction intervals enables the user to employ and tolerate greater traction weight than would be possible if non-cyclical cervical (static) traction were employed. The cyclic mode of operation is usually chosen by the physician or therapist. The greater traction weight is desirable as it accomplishes greater extension of the neck region which provides enhanced therapeutic benefits.

In various instances, cyclical or intermittent cervical traction may not be necessary or warranted. In such situations, the non-cyclical device as shown in FIG. 4 can be employed. When the non-cyclical device is employed, the patient-user is placed in position and tractive force is applied to the neck region for a continuous interval. As with the cyclical cervical traction device described previously, the amount of tractive force and the total cervical traction interval are patient specific and should be recommended by a physician, physical therapist, or other qualified health care professional on a case-by-case basis based on individual needs and requirements.

In either situation, use of either the cyclic, intermittent, or non-cyclic cervical traction device of the present invention permits the patient-user to engage in cervical traction at home or where convenient. Thus, cervical traction therapy can be performed more frequently.

The increased therapy frequency has the potential of reducing the total time the patient would require therapy and providing benefits to the patient such as an alleviation of pain in a shorter period of time. Use of the cervical traction unit of the present invention in the home provides the additional advantage in that the patient can obtain a clinical equivalent of cervical traction when needed during the day at home rather than waiting until the next scheduled visit to the physical therapist. Prompt alleviation of pain and discomfort can prevent further patient debilitation and can actually promote healing in some instances. Additionally, the ability to employ cervical traction as needed can actually assist in the restoration of normal sleep patterns as cervical traction can be performed in bed immediately prior to sleep. The unit can be removed while the patient is in the supine position thereby preventing the affected region from experiencing a potentially painful compressive load prior to sleep.

In situations where the cyclical traction unit of the present invention is employed, and because the cervical traction device is user operated, the cycled application and release of tractive force during a therapy session is controlled by the patient. Because of this, the application and release of tractive force can be uniquely attuned to the physical indications experienced during each treatment session. Such patient control can provide subtle advantageous modifications of the general therapy regimen with each cycle in response to the physical conditions experienced. Such fine variations cannot be duplicated by a static unit or by an externally controlled device. Additionally, control of the tractive force cycle by the patient can have significant psychological benefits due to the restoration of control to the patient of at least one area of his health and well being after a period of disability. Finally, the cervical traction device of the present invention makes it possible for the patient-user to perform cyclic therapy using maximum tractive force multiple times during the course of a day or week in the comfort and privacy of his own surroundings.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A cervical traction device for use on a support surface providing cycling tractive force to the neck and head region of a patient-user comprising:

a head rest assembly positioned on the support surface at an angle between 0° and 40° from horizontal having means for releasably contacting the skull of the patient-user proximate to the occipital region of the skull;

means for providing tractive force to the skull through the head rest assembly;

a tractive force transferring system comprising:

a) a tension line providing connection between the head rest assembly and the tractive force providing means; and b) means for cylindery varying the amount of tractive force exerted on the skull by the tractive force providing means from a first tractive force level equal to zero to a second tractive force level greater than the first tractive force level, wherein the means for cyclically varying the amount of tractive force comprises:

a) a pulley device through which the tension line extends and is moveable relative thereto such that the tension line defines a first leg between the head rest assembly and the pulley device and a second leg between the pulley device and the means for providing tractive force; and b) a tension release line having a first end and second end, the first end connected to the first leg of the tension line between the pulley device and the head rest, the second end of the tension release line terminating in means for releasably contacting an appendage of the patient; and c) means for dampening transfer of force from the tension release line to the head rest assembly, the dampening means comprising a shock prevention load dampening device positioned between the pulley device and the tractive force exerting means.

2. The tractive force transferring system of claim 1 wherein the shock prevention load dampening device further comprises a gas cylinder having an outer body attached to the pulley device and an inner rod telescopically received in the outer body, the inner rod having a distal end connected to the tractive force providing means wherein reduction of length of the second leg of the tension line results in retraction of the inner rod into the outer cylinder, and increase in the length of the second leg of the tension line due to action of the tractive force providing means results in a dampened telescopic extension of the inner rod; and means for limiting maximum compression of said gas cylinder which results in a fully dampened stroke.

3. The cervical traction device of claim 1 further comprising means for limiting tractive force load exerted on the head rest assembly.

4. The cervical traction device of claim 3 wherein the tractive force load limiting means comprises:

a magnetic member having a magnetic attractive force less than a predetermined maximum; and a mating attractive member releasably contactable with the magnetic member, the magnetic member and the attractive member positioned in the tension transfer line between the head rest assembly and the weight means.

5. The cervical traction device of claim 1 wherein the base of the head rest assembly is positioned at an angle about 0° and about 30° from horizontal.

6. The cervical traction device of claim 1 wherein the head rest assembly is adjustable to a lateral angle between about 0° and about 20° from an axis extending through the cervical neck region of the patient.

7. The cervical traction device of claim 1 wherein the means for exerting tractive force on the head rest assembly comprises;

an adjustable weight member; and a hook device connected to the adjustable weight member, the hook device connected to the tractive force transferring system.

8. The cervical traction device of claim 1 wherein the adjustable weight member comprises:

an outer housing defining a hollow interior region, the outer housing having at least one aperture defined therein; and a cap closably overlying the aperture in the outer housing.

9. The cervical traction device of claim 1 wherein the head rest comprises:

a base having an upper face and an opposed lower face, the upper face adapted to receive the cranial region of the skull of the patient, the base also having a first end adapted to be positioned proximate to the neck region of the patient and an opposed second end, the lower face adapted to directly contact and cyclically slide on the support surface; and a pair of members mounted on the base and protruding upward therefrom, the pair of upwardly protruding members positioned proximate to the first end of the base, the upwardly protruding members having a height and contour sufficient to releasably contact the skull of the patient proximate to the occipital region while the cranial region is proximate to the upper face of the base.

10. The cervical traction device of claim 9 wherein the head rest assembly further comprises means for positioning the base relative to the underlying support surface, the head rest assembly positioning means comprising a bolster device interposed between the elevated support and the lower face of the head rest assembly.

11. The cervical traction device of claim 9 wherein the upwardly protruding members of the head rest assembly each comprise:

a first outer edge extending outward from the base of the head rest assembly;

a second lower edge oriented relative to the first outer edge, the second lower edge joinably contacting the base; and a third edge contiguous to the second lower edge oriented to receive and support the portion of the patient's skull proximate to the occipital region;

wherein the upwardly protruding members are positioned on the base symmetrically relative to one another.

12. The cervical traction device of claim 11 further comprising a friction reduction member contacting the lower face of the base of the head rest assembly.

13. The cervical traction device of claim 9 wherein the head rest assembly further comprises:

means for adjustably positioning the upwardly protruding members relative to one another; and a deformably contourable skull receiving member positioned on the upper face of the base of the head rest assembly at a location suitable for receiving the posterior cranial region of the patient's skull.

14. The cervical traction device of claim 1 wherein the base of the head rest assembly further comprises a forward edge located proximate to the first end, the foward edge having a geometric profile capable of facilitating slidable movement of the head rest assembly on the support.

15. A cervical traction device for use on a support surface providing cycling tractive force to the neck and head region of a patient-user comprising:

a head rest assembly positioned on the support surface at an angle between 0° and 40° from horizontal having means for releasably contacting the skull of the patient-user proximate to the occipital region of the skull;

means for providing tractive force to the skull through the head rest assembly;

a tractive force transferring system comprising:

a) a tension line providing connection between the head rest assembly and the tractive force providing means; and b) means for intermittently varying the amount of tractive force exerted on the skull by the tractive force providing means from a first tractive force level greater than zero to a second tractive force level greater than the first tractive force level, wherein the means for varying the amount of tractive force comprises:

a) a first pulley device through which the tension line extends and is moveable relative thereto such that the tension line defines a first leg between the head rest assembly and the first pulley device;

b) a second pulley device through which the tension line extends and is moveable relative thereto such that the tension line defines a second leg between the first pulley device and the second pulley device, wherein the means for providing tractive force on the head rest assembly is attached to the second pulley device and wherein the tension line extends back though the first pulley device thereby defining a third leg therein;

c) a tension release line being the third leg of the tension line proximate to the first pulley device and a second end, the second end of the tension release line terminating in means for releasably contacting an appendage of the patient;

d) a shock prevention load dampening device comprising a gas cylinder having an outer body attached to the first pulley device and an inner rod telescopically received in the outer body, the inner rod having a distal end in connection with tractive force providing means wherein reduction of length of the second leg of the tension line results in retraction of the inner rod into the outer cylinder and increase in the length of the second leg of the tension line due to action of the tractive force providing means results in a dampened telescopic extension of the inner rod; and e) means for limiting maximum compression of said gas cylinder which results in a fully dampened stroke.

16. The cervical traction device of claim 15 wherein the tractive force transferring system further comprises:

a first stop member positioned in the first leg of the tension line, the first stop member releasably contactable with the second pulley device, the first stop member positioned in the first leg of the tension transfer line such that extension of the tension release line results in contact between the between the first stop member and the second pulley device; and a second stop member positioned in the third leg of the tension line, the second stop member releasably contactable with the second pulley device.

17. The tractive force transferring system of claim 16 further comprising means for limiting transfer of tractive force load from the tractive force exerting means to the head rest assembly.

18. The cervical traction device of claim 15 wherein the base of the head rest assembly is positioned at an angle about 0° and about 30° from horizontal.

19. The cervical traction device of claim 15 wherein the head rest assembly is adjustable to a lateral angle between about 0° and about 20° from an axis extending through the cervical neck region of the patient.

20. The cervical traction device of claim 15 wherein the means for exerting tractive force on the head rest assembly comprises;

an adjustable weight member; and a hook device connected to the adjustable weight member, the hook device connected to the tractive force transferring system; and wherein the adjustable weight member comprises:

an outer housing defining a hollow interior region, the outer housing having at least on aperture defined therein; and a cap closeably overlying the aperture in the outer housing.

21. The cervical traction device of claim 15 wherein the head rest assembly comprises:

a base having an upper face and an opposed lower face, the base of the head rest assembly further having a first end adapted to be positioned proximate to the neck region of the patient-user, the first end having a forward edge extending from the upper face to the lower face, the forward edge contactable with the support surface, the base further having a second end opposed thereto, the tension line attached to the base proximate to the second end; and a pair of members mounted on the base and extending upward therefrom, the pair of upwardly extending members position proximate to the first end of the base, the upwardly extending members configured to releasably contact the skull of the patient-user proximate to the occipital region.

22. The cervical traction device of claim 21 wherein the head rest assembly further comprises means for positioning the base relative to the underlying support surface, the head rest assembly positioning means comprising a bolster device interposed between the elevated support and the lower face of the head rest assembly.

23. The cervical traction device of claim 21 wherein the upwardly extending members of the head rest assembly each comprise:

a first outer edge extending outward from the base of the head rest assembly;

a second lower edge oriented relative to the first outer edge, the second lower edge joinably contacting the base; and a third edge contiguous to the second lower edge oriented to receive and support the portion of the patient's skull proximate to the occipital region;

wherein the upwardly protruding members are positioned on the base symmetrically relative to one another.

24. The cervical traction device of claim 23 further comprising a friction reduction member in contact with the lower face of the base of the head rest assembly.

25. The cervical traction device of claim 23 wherein the head rest assembly further comprises:

means for adjustably positioning the upwardly protruding members relative to one another; and a deformably contourable skull receiving member positioned on the upper face of the base of the head rest assembly at a location suitable for receiving the posterior cranial region of the patient's skull.

26. The cervical traction device of claim 15 wherein the base of the head rest assembly further comprises a forward edge located proximate to the first end, the forward edge having a geometric profile capable of facilitating slidable movement of the head rest assembly on the support.

27. A cervical traction device for use on a support surface providing cycling tractive force to the neck and head region of a patient-user comprising:

a head rest assembly positioned on the support surface at an angle between 0° and 40° from horizontal having means for releasably contacting the skull of the patient-user proximate to the occipital region of the skull;

means for providing tractive force to the skull through the head rest assembly;

a tractive force transferring system comprising:

A) a tension line providing connection between the head rest assembly and the tractive force providing means; and B) means for intermittently varying the amount of tractive force exerted on the skull by the tractive force providing means from a first tractive force level greater than zero to a second tractive force level greater than the first tractive force level, wherein the means for varying the amount of tractive force comprises:

i) a first pulley device through which the tension line extends and is moveable relative thereto such that the tension line defines a first leg between the head rest assembly and the first pulley device;

ii) a second pulley device through which the tension line extends and is moveable relative thereto such that the tension line defines a second leg between the first pulley device and the second pulley device, wherein the means for exerting tractive force on the head rest assembly is attached to the second pulley device and wherein the tension line extend back though the first pulley device thereby defining a third leg therein;

iii) a tension release line being the third leg of the tension line proximate to the first pulley device and a second end, the second end of the tension release line terminating in means for releasably contacting an appendage of the patient; and C) means for limiting transfer of tractive force load from the tractive force exerting means to the head rest assembly, the tractive force load limiting means comprising:

i) a magnetic member having a magnetic attractive force greater than the maximum allowable tractive force to be transferred;

ii) a mating attractive member releasably contactable with the magnetic member, the magnetic member and the attractive member positioned in the system between the head rest assembly and the weight means.

28. The cervical traction device of claim 27 wherein the head rest assembly comprises:

a base having an upper face and an opposed lower face, the base of the head rest assembly further having a first end adapted to be positioned proximate to the neck region of the patient-user, the first end having a leading surface extending from the upper face to the lower face, the leading surface contactable with the support surface, the base further having a second end opposed thereto, the tension line attached to the base proximate to the second end;

a pair of members mounted on the base and extending upward therefrom, the pair of upwardly extending members position proximate to the first end of the base, the upwardly extending members configured to releasably contact the skull of the patient-user proximate to the occipital region; and means for positioning the base relative to the underlying support surface, the head rest assembly positioning means comprising a bolster device interposed between the elevated support and the lower face of the head rest assembly;

wherein the base of the head rest assembly further comprises a forward edge located proximate to the first end, the pivot surface having a geometric profile capable of facilitating slidable movement of the head rest assembly on the support.

* * * * *